(12) United States Patent
Cook

(10) Patent No.: US 12,582,671 B1
(45) Date of Patent: Mar. 24, 2026

(54) WATER SOLUBLE ELECTROLYZED SILICON DIOXIDE FORMULATION AND METHOD OF MANUFACTURE

(71) Applicant: Christina Rahm Cook, Brentwood, TN (US)

(72) Inventor: Christina Rahm Cook, Brentwood, TN (US)

( * ) Notice: Subject to any disclaimer, the term of this patent is extended or adjusted under 35 U.S.C. 154(b) by 433 days.

(21) Appl. No.: 18/372,897

(22) Filed: Sep. 26, 2023

Related U.S. Application Data

(63) Continuation-in-part of application No. 17/529,400, filed on Nov. 18, 2021, now abandoned.

(51) Int. Cl.
| | |
|---|---|
| *A61K 33/00* | (2006.01) |
| *A61K 31/355* | (2006.01) |
| *A61K 31/375* | (2006.01) |
| *A61K 31/593* | (2006.01) |
| *A61K 33/04* | (2006.01) |
| *A61K 33/26* | (2006.01) |
| *A61K 33/30* | (2006.01) |
| *C01B 33/18* | (2006.01) |

(52) U.S. Cl.
CPC ............ *A61K 33/00* (2013.01); *A61K 31/355* (2013.01); *A61K 31/375* (2013.01); *A61K 31/593* (2013.01); *A61K 33/04* (2013.01); *A61K 33/26* (2013.01); *A61K 33/30* (2013.01); *C01B 33/18* (2013.01)

(58) Field of Classification Search
CPC .... A61K 33/00; A61K 31/355; A61K 31/375; A61K 31/593; A61K 33/04; A61K 33/26; A61K 33/30; C01B 33/18
See application file for complete search history.

(56) References Cited

FOREIGN PATENT DOCUMENTS

WO       WO 2008138737       * 11/2008    ........... H10F 71/121

* cited by examiner

*Primary Examiner* — Robert A Wax
*Assistant Examiner* — John Seungjai Kwon
(74) *Attorney, Agent, or Firm* — Gulf Coast Intellectual Property Group

(57)                ABSTRACT
The present invention relates generally to water soluble formulations for materials such as pharmaceuticals and nutraceuticals. The present invention includes a method and a formulation of bio-available silicon dioxide fragments combined with vitamins, amino acids, nutrient compounds, and minerals that can be utilized to detoxify, replenish and stimulate growth in living organisms providing benefits such as but not limited to improvements in the aging process. The formulation of the present invention is a water-soluble electrolyzed silicon dioxide formulation operable to provide intracellular detoxification wherein the composition of the present invention can further include minerals or vitamins. The water soluble electrolyzed silicon dioxide formulation of the present invention is operable to provide intracellular detoxification wherein the water-soluble hydrolyzed silicon dioxide fragments can be complexed with a metal ion. The formulation is provided in liquid capsules, slurry form, gels or syrups.

8 Claims, 4 Drawing Sheets

WATER SOLUBLE ELECTROLYZED SILICON DIOXIDE FORMULATION AND METHOD OF MANUFACTURE

CROSS REFERENCE TO RELATED APPLICATIONS

This application is a continuation-in-part of U.S. patent application Ser. No. 17/529,400 filed, Nov. 18, 2021, entitled, Water Soluble Electrolyzed Silicon Dioxide Formulation, in the name of Christina Rahm Cook, which is hereby incorporated for reference.

FIELD OF THE INVENTION

The present invention relates generally to partially water soluble formulations for materials such as pharmaceuticals and nutraceuticals, more specifically but not by way of limitation, a formulation of bio-available silicon dioxide fragments combined with vitamins, amino acids, nutrient compounds, and minerals that can be utilized to detoxify, replenish and stimulate growth in living organisms providing benefits such as but not limited to improvements in the aging process.

BACKGROUND

Silicon dioxide, also known as silica, is an oxide of silicon with the chemical formula $SiO_2$. Silicon dioxide is most commonly found in nature as quartz and in various living organisms. Silicon dioxide is used to structure materials and is often utilized in the food and pharmaceutical industries. Quartz, Silica, Silicic oxide, Crystalline silica, Silicea, Silica sand (also known as Silicon dioxide) is a large group of minerals of hydrated aluminosilicates of sodium, potassium, calcium, and barium. There have been attempts to create commercially available nutraceutical products that have included simple water suspensions of silicon dioxide but none have been able to successfully break down the minerals to allow silicon dioxide to be absorbed intracellularly. These products fail to bring silicon dioxide's ability to remove heavy metals into the cell, referred to as in vivo. Existing technology and attempts to enable intracellular absorption have failed as silicon dioxide and various forms of silica compounds are non-water soluble having a three-dimensional honeycomb configuration.

Silicon dioxide binds heavy metals naturally. Existing technology fails to bring silicon dioxide's ability to remove heavy metals, toxins, viral particles, and certain bacteria in vivo. These heavy metals include, but are not limited to mercury, cadmium, arsenic, lead, cesium, strontium, uranium, tin, copper, gadolinium, thallium, thorium, antimony, iron, platinum, chromium, barium, beryllium, methane, greenhouse cases, nitrogen, ammonia, aflatatoxin, melamine, and nitrosamine. As quartz, silicon dioxide and other silica-based compounds are non-water soluble, non-bio-available salt with a three dimensional negatively charged honeycomb configuration results in a naturally insoluble material and cannot work effectively to detoxify human cells. Additionally, existing technology fails to provide effective cross the blood-brain barrier so as to potentially detoxify and replenish cells. The blood brain barrier protects the neural tissue from variations in blood composition and toxins. Elsewhere in the body the extracellular concentrations of hormones, amino acids and potassium undergo frequent fluctuations, especially after meals, exercise or stressful times. Since many of these molecules regulate neuronal excitability, a similar change in the composition of interstitial fluid in the central nervous system can lead to uncontrolled brain activity. The endothelial cells forming the blood-brain barrier are highly specialized to allow precise control of the substances that enter or leave the brain.

Accordingly, there is a need to create water-soluble silicon dioxide formulations, which can be administered and absorbed in vivo to detoxify and replenish minerals in the human body.

SUMMARY OF THE INVENTION

It is the object of the present invention to provide a water soluble electrolyzed silicon dioxide formulation operable to provide intracellular detoxification wherein the present invention includes compositions and methods enabling formation and use of a water-soluble and bio-available silicon dioxide employing various forms of electrolysis producing a product to be used as supplement configured to provide cellular detoxification.

Another object of the present invention is to provide a composition containing water soluble silicon dioxide fragments operable to absorb toxins such as but not limited to heavy metals wherein the composition of the present invention includes water-soluble electrolyzed silicon dioxide fragments and water-soluble hydrolyzed silicon dioxide fragments with a dietary supplement such as but not limited to vitamins, minerals, fiber, fatty acid, amino acid, herb, herbal extract or combinations thereof.

A further object of the present invention is to provide a water soluble electrolyzed silicon dioxide formulation operable to provide intracellular detoxification wherein the methods of the present invention include performing a primary hydrolysis reaction by hydrolyzing silicon dioxide with or without electrolysis with an acid and separating the primary hydrolysis reaction into a first liquid portion and a first solid portion wherein the first liquid portion includes a primary hydrolysis reaction product including water-soluble hydrolyzed silicon dioxide fragments.

Still another object of the present invention is to provide a composition containing water soluble silicon dioxide fragments operable to absorb toxins such as but not limited to heavy metals wherein the method of the present invention includes a secondary hydrolysis and electrolysis reaction that is performed by hydrolyzing and/or electrolyzing the first solid portion with additional silicon dioxide with an acid. Furthermore, the secondary hydrolysis reaction can be separated into a second liquid portion and a second solid portion with the second liquid portion including a secondary hydrolysis reaction product including water-soluble hydrolyzed silicon dioxide fragments.

An additional object of the present invention is to provide a water soluble electrolyzed silicon dioxide formulation operable to provide intracellular detoxification wherein the water-soluble hydrolyzed silicon dioxide fragments can be complexed with a metal ion, wherein the metal ion can include a member selected from the group consisting of sodium, magnesium, iron, cobalt, copper, zinc, manganese, molybdenum, selenium or combinations thereof.

Yet a further object of the present invention is to provide a composition containing water soluble silicon dioxide fragments operable to absorb toxins such as but not limited to heavy metals wherein the composition can further include a dietary supplement wherein the supplements can reduce fat mass and further promote weight loss resulting from the detoxification of the cells.

Another object of the present invention is to provide a water soluble electrolyzed silicon dioxide formulation operable to provide intracellular detoxification wherein the present invention includes water-soluble hydrolyzed silicon dioxide fragments that can be prepared by a process combining hydrolyzed silicon dioxide with an acid such as but not limited to phosphoric acid and further includes separating the hydrolyzed silicon dioxide into a liquid portion and a solid portion.

Still an additional object of the present invention is to provide a composition containing water soluble silicon dioxide fragments operable to absorb toxins such as but not limited to heavy metals wherein the composition can further include a pharmaceutical product, wherein the pharmaceutical product is operable for use as a delivery mechanism for a second pharmaceutical compound.

Yet another object of the present invention is to provide a water soluble electrolyzed silicon dioxide formulation operable to provide intracellular detoxification wherein the composition of the present invention can further include a mineral or vitamin selected from the group consisting of selenium, zinc, sulfur, iron, vitamin B, vitamin C, vitamin E, vitamin D, retinol or any combination thereof.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
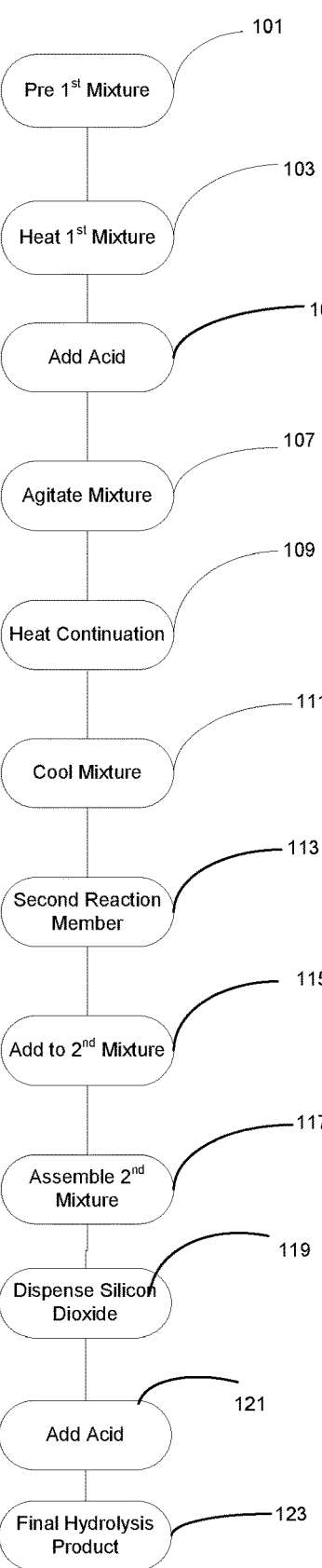
FIG. 1 is a diagrammed outline of a primary hydrolysis reaction of the present invention.

Referring now to the drawings submitted herewith, wherein various elements depicted therein are not necessarily drawn to scale and wherein through the views and figures like elements are referenced with identical reference numerals, there is illustrated a silicon dioxide formulation and method of manufacture 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Generally, hydrolysis is a process by which a bond in a particular molecule is broken, and an O—H bond in a water molecule also breaks. Then, from the water molecule, an O—H group adds to one part from the particular molecule, and an H atom is added to the other part of the particular molecule. A similar process can be performed using a different solvent other than, or in addition to, water, such as an alcohol such as methanol, ethanol, ammonia, a glycol, or an amine. Such general processes are referred to as solvolysis process. When the solvent is water, the process is hydrolysis. When the solvent is an alcohol, this process is an alcoholysis process. When the solvent is ammonia, the process is an ammonolysis process. When the solvent is glycol, the process is a glycolysis process. When the solvent is an amine, the process is an aminolysis process. Silicon dioxide is partially soluble due to the fact that the electron thereof are positioned tightly between atoms and generally immovable. Silicon dioxide is not one hundred percent soluble in water or organic solvents. There is not a possible attraction that can occur between solvent molecules and silicon or oxygen atoms that can overcome the covalent bond in the silicon dioxide structure. Silicon dioxide has a water solubility of 0.12 g/L whereas silicon carbide is water soluble. As is further discussed herein, silicon is part of various minerals and can be released under different manufacturing processes as it is released in nature during weathering processes. A step contemplated within the scope of the present invention includes dissolving silica in hot concentrated sodium or potassium hydroxide solution. The aforementioned dissolves alumina and other elements as well. Additionally, hydrofluoric acid (HF) can be utilized and mixtures of HF with Hydrochloric acid (HCl), Sulfuric acid or Nitric acid.

Referring in particular to the Figures submitted as a part hereof, present technology includes water-soluble hydrolyzed silicon dioxide fragments, compositions and methods of making hydrolyzed silicon dioxide fragments. Reference herein to hydrolyzed silicon dioxide fragments includes water-soluble hydrolyzed silicon dioxide fragments. Silicon dioxide can include a natural quartz, silica, silicic oxide, silicon (IV) oxide, crystalline silica, pure silica, silicea, silica sand with a microporous arrangement of silica and alumina tetrahedral. Silicon dioxide (aluminum sodium dioxido (oxo) silane) can be referred to as sodium aluminosilicate or aluminum sodium silicate. The structure of silicon dioxide can include an outer framework of silica and alumina tetrahedral within which water molecules and exchangeable cations can migrate. An hydrolyzed silicon dioxide fragment concentrate can generally be produced as follows. A two-stage hydrolysis reaction is utilized to produce the hydrolyzed silicon dioxide fragments concentrate, which includes a primary hydrolysis reaction and a secondary hydrolysis reaction. In certain embodiments, the process can be carried out over several days. The primary hydrolysis reaction can be performed over approximately a twenty four hour time period. The primary hydrolysis product is recovered by siphoning and filtering the product. The secondary hydrolysis reaction is performed and the secondary hydrolysis product can also be recovered by siphoning and filtering the product. Electrolysis can be used before the primary and secondary hydrolysis process.

The primary hydrolysis reaction includes the following steps. In step 101, a first reaction mixture can be prepared including silicon dioxide, phosphoric acid, and water. Step 103, the first reaction mixture is assembled by heating the water and adding the silicon dioxide while agitating the first reaction mixture and further dispensing one of the following thereinto: quartz, silica, silicic oxide, silicon (IV) oxide, crystalline silica, pure silica, silicea, silica sand. The aforementioned are dispensed at a rate that minimizes clumping in order to form a relatively uniform slurry. In step 105, the phosphoric acid is added to the silicon dioxide-water mixture. It should be understood within the scope of the present invention that the addition of the phosphoric acid can be at a rate that maintains a desired temperature profile for the first reaction mixture. Step 107, agitation is executed to maintain the first reaction mixture as a slurry during the phosphoric acid addition. In step 109, heating is continued for completion of the primary hydrolysis reaction. Step 111, ensuring completion of the primary hydrolysis reaction, the first reaction mixture is cooled to ambient temperature. Completion of the primary hydrolysis reaction can be monitored as follows. At various time intervals, agitating and heating of the first reaction mixture can be stopped. Morphology of the mixture surface can be observed, where gas production and release through the mixture can indicate that the primary hydrolysis reaction may not be complete. Agitation of the first reaction mixture can continue if the primary hydrolysis reaction is not yet complete. The primary hydrolysis reaction and monitoring thereof can be continued until gas production and release through the mixture surface are no longer observed or has substantially depleted.

Once the primary hydrolysis reaction is cooled to ambient temperature the first reaction mixture is allowed to settle. Settling results in two layers including a first substantially liquid layer and a solid layer. It is the first liquid layer that includes the primary hydrolysis reaction product. The first liquid layer is separated from the first solid layer by siphoning, decanting or other suitable process. The first liquid layer can be further filtered to obtain a substantially transparent liquid. The first liquid layer is stored thereafter wherein storage includes refrigeration of the first liquid layer. The first liquid layer including the primary hydrolysis reaction product can be characterized with the following. The first liquid layer has an acidic pH and a solid portion, wherein a solid portion of about 1-25 mg/ml, including about 18-22 mg/ml. In step 113, a second reaction mixture is formed that includes the first solid layer from the primary hydrolysis reaction. Step 115, to the second reaction mixture silicon dioxide, phosphoric acid, and water are added. Step 117, the second reaction mixture is assembled by heating the water and the first solid layer from the primary hydrolysis reaction and further adding silicon dioxide while agitating the second reaction mixture. In step 119, dispensing silicon dioxide at a rate that minimizes clumping in order to form a relatively uniform slurry. Step 121, phosphoric acid is added to the mixture of the first solid layer, water, and silicon dioxide. Addition of the phosphoric acid is at a rate that maintains a desired temperature profile for the second reaction mixture, where agitation can maintain the second reaction mixture as a slurry during the phosphoric acid addition. Heating can be continued as necessary for completion of the secondary hydrolysis reaction. Once completed, the second reaction mixture is cooled to ambient temperature. In step 123, the first liquid layer of the primary hydrolysis reaction and the second liquid layer of the secondary hydrolysis reaction are combined to make a final hydrolysis product. The final hydrolysis product can be characterized as follows. The final hydrolysis product can have an acidic pH, for example, a pH that can range from 4.5 to 5.5.

Hydrolyzed silicon dioxide fragments can be diluted to desired amounts or percentages by weight. By way of example but not limitation, the final hydrolysis product obtained using the methods described herein can have a solid portion of about 15-25 mg/ml, corresponding to 1.5-2.5% by weight. Dilution can be with sterile, distilled or deionized water. Solutions of the hydrolyzed silicon dioxide fragments and water used to dilute the hydrolyzed silicon dioxide fragments also include various stabilizers and/or preservatives. For example, sodium benzoate or potassium sorbate can be utilized. The water-soluble nature of the hydrolyzed silicon dioxide fragments provides certain benefits when administering the hydrolyzed silicon dioxide fragments. By way of example but not limitation, oral administration of the hydrolyzed silicon dioxide fragments results in gastrointestinal absorption of at least a portion of the hydrolyzed silicon dioxide fragments. The absorbed hydrolyzed silicon dioxide fragments pass into the blood and are transported to areas of the body providing benefits that include but are not limited to binding of heavy metals and environmental toxins, absorption at the cellular level, passing into adipose tissue where heavy metals can accumulate or stored within adipose tissue, reduction of reactive oxygen species and inflammation related thereto, providing an increase in energy and providing an increase in focus, concentration and memory.

The hydrolyzed silicon dioxide fragments can be used alone and can be used as a component in various compositions that include one or more various dietary supplements, such as one or more various vitamins and/or one or more various nutraceuticals. Non-limiting examples of dietary supplements further include vitamins, minerals, fiber, fatty acids, amino acids, herbs, herbal extracts, and combinations thereof. In certain embodiments, such dietary supplements are not intended to diagnose, treat, cure, or prevent any disease. The composition can include one or more food ingredients or foods. The hydrolyzed silicon dioxide fragments can be combined or complexed with various ions, including various metals, in order to provide a water-soluble source of the ions. Examples include calcium, potassium, sodium, magnesium, iron, cobalt, copper, zinc, manganese, molybdenum, selenium, and combinations thereof. The hydrolyzed silicon dioxide fragments can also be used to chelate or scavenge various metals, including toxic metals, where the hydrolyzed silicon dioxide fragments can facilitate detoxification. In certain embodiments, the hydrolyzed silicon dioxide fragments can be combined with vitamin C including various salts, derivatives, and esters thereof. Vitamin C receptors exist in endothelial cells in the human body. The number of vitamin C receptors can also be significantly increased in endothelial cells that are part of the blood-brain barrier.

The composition of the present invention including the hydrolyzed silicon dioxide fragments can be formulated in various ways, typically for oral administration. Examples include forming the composition into one or more various liquid capsules, providing the composition in a liquid or slurry form, and providing the composition as a gel or syrup. Composition components can be entirely mixed together into a single portion, each provided as a separate portion, or various components can be admixed where the whole composition is provided by more than one portion but where a total number of portions are less than the number of components. Other dosage forms suitable for oral administration can be used. In some embodiments, the water-soluble hydrolyzed silicon dioxide fragments are formulated for other routes of administration, such as but not limited to topical, inhalation and injection.

Figure 2:
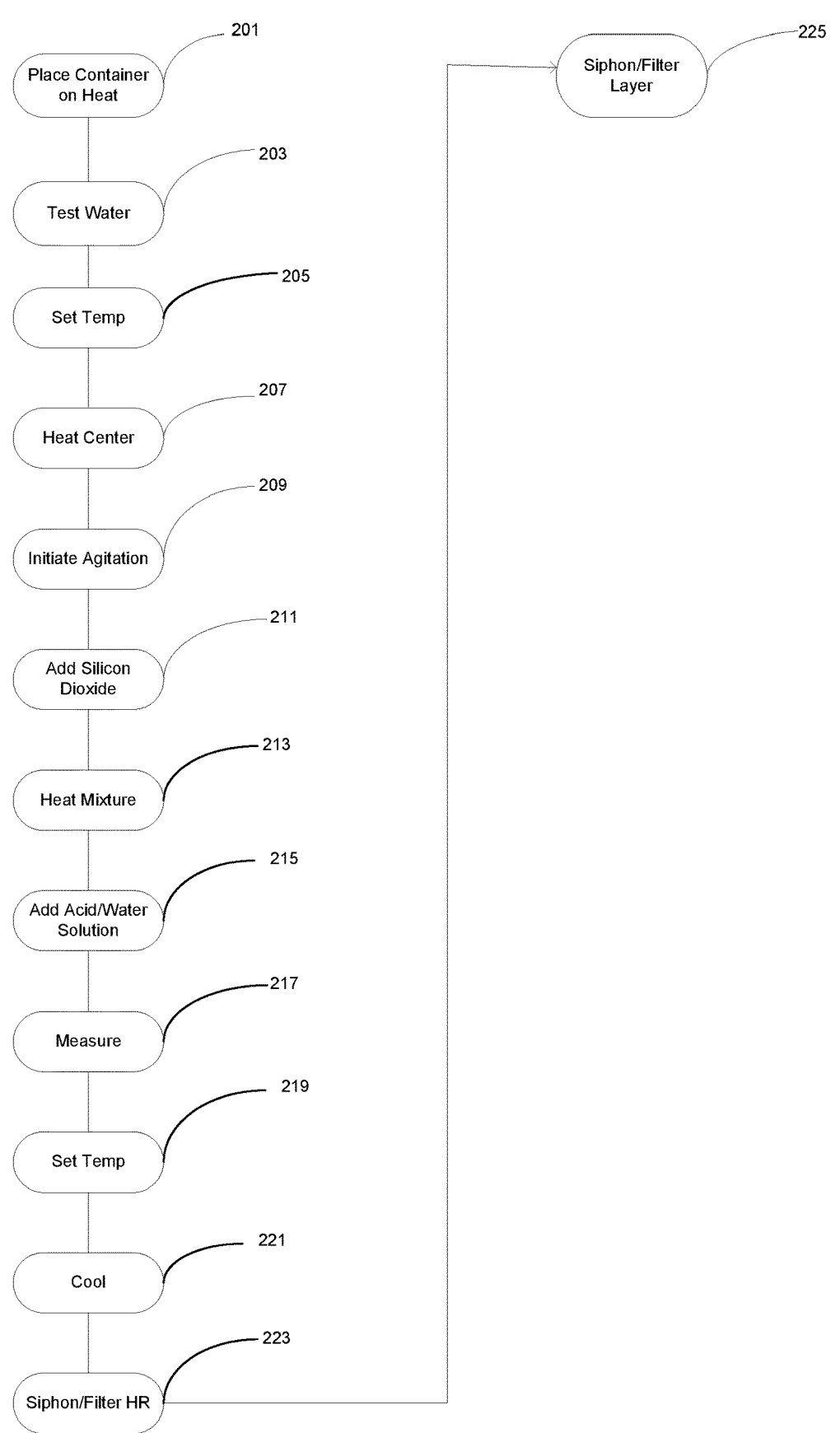
FIG. 2 is an outline of the processing procedure of the primary reaction of the present invention.

Referring now to FIG. 2, an outline of processing the primary hydrolysis reaction is diagrammed therein. Step 201, place a suitable container on a heating plate and test variant degrees of temperatures. In step 203, test ultra-violet treated reverse osmosis water and untreated reverse osmosis water in the container. In step 205, set the heating plate should be set between 100 and 200° F. Step 207, water is heated to 150-200° F. In step 209, once the water temperature reaches between 125 and 175° F., stirring should be initiated. Step 211, once water temperature reached 150-200° F., silicon dioxide is transferred slowly to the container with consistent agitation during this process. Step 213, heat the silicon dioxide water mixture to a temperature between 150-200 degrees Fahrenheit. In step 215, add between one hundred and fifty and two hundred milliliters of a phosphoric acid/water solution to the silicon dioxide-water mixture. Step 217, measure the time-point of the primary hydrolysis reaction. In step 219, set the heating plate temperature to a range between 400 and 600° F. Step 221, remove the container with the mixture from the heating plate and cool at room temperature for twenty four hours. Monitoring of the progression of the hydrolysis reaction with or without electrolysis. The electrolysis process can be monitored with variant degrees of energy and the hydrolysis reaction progression is monitored qualitatively using the following exemplary techniques. Every 10-15 minutes after time-point zero for an hour for testing, the stirring should be stopped for 10 to 30 seconds and the surface of the Heating Plate was should be set to zero to 10. The morphology of the mixture surface should be observed. Monitor and note the gas production and release through the mixture surface to see if the primary hydrolysis reaction was not completed. If the primary hydrolysis reaction was not completed, the heating plate temperature should be set again be 400-600° F. and stirring should be re-initiated. The aforementioned process should be repeated until gas production and release through the mixture surface is observed. This indicates completion of the primary hydrolysis reaction.

In step 223, siphon and filter the primary hydrolysis reaction product and cool for twenty four hours at ambient temperature. Two distinct layers will form in the container as the result of the primary hydrolysis reaction, a liquid layer and a solid product layer. Step 225, siphon and filter the liquid layer and transfer liquid to cool storage container. The quantitative characteristics of the primary hydrolysis reaction product are as follows: Volume: 2,700±500 ml; pH 4.8 to 4.9 and solids of 18-22 mg/ml.

Figure 3:
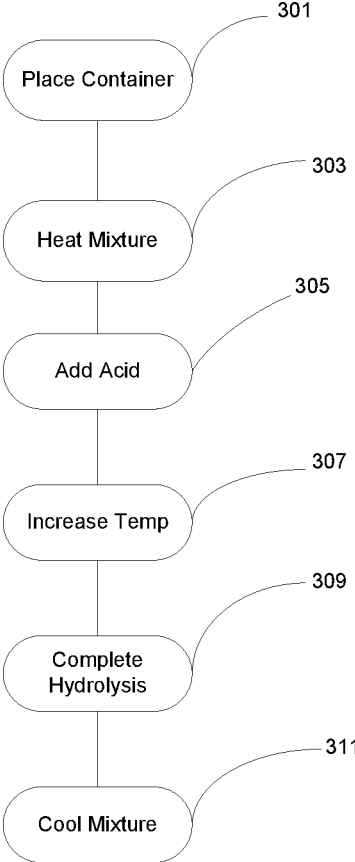
FIG. 3 is an outline of the secondary hydrolysis reaction of the present invention.

Referring now to FIG. 3 submitted herewith, the processing of the secondary hydrolysis reaction is outlined therein. In step 301, the container from the primary hydrolysis reaction having the solid layer disposed therein along with material added for the secondary hydrolysis reaction is placed on a heating plate. Step 303, set heating plate at 190° F. and heat mixture until the mixture temperature becomes 170-185° F. In step 305, add phosphoric acid/water solution. This time-point of the secondary hydrolysis reaction is defined as time-point zero. Step 307, once the phosphoric acid/water solution is added to the mixture, the heating plate temperature is set to 500 degrees Fahrenheit. In step 309, the mixture can be further heated as needed for the completion of the secondary hydrolysis reaction. Step 311, subsequent the secondary hydrolysis reaction being completed, the mixture is cooled to ambient temperature.

Figure 4:
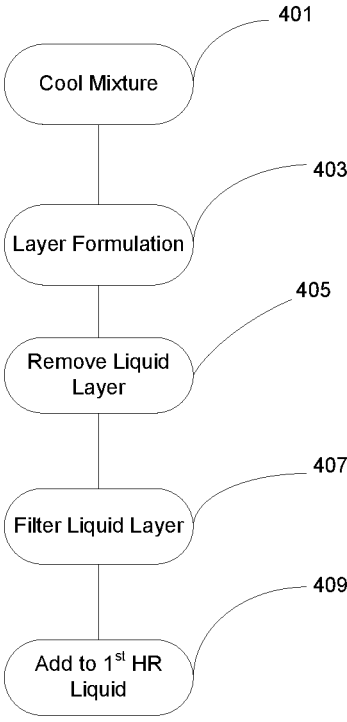
FIG. 4 is an exemplary treatment process of the secondary reaction product of the present invention.

FIG. 4 submitted herewith diagrams therein an outline for the treatment of the secondary hydrolysis reaction product. Step 401, the mixture from the secondary hydrolysis reaction is cooled for twenty-four hours. In step 403, formation of distinct layers are formed in the container as the result of the secondary hydrolysis reaction, a liquid layer and a solid product layer. Step 405, the liquid layer is siphoned off so as to separate from the solid layer. In step 407, liquid product is filtered as needed. Step 409, the liquid product from the primary hydrolysis reaction is added to the liquid product from the secondary hydrolysis reaction. It should be understood within the scope of the present invention that the quantitative characteristics of the secondary hydrolysis reaction product are similar to those of the primary hydrolysis reaction product.

The following is an exemplary process of a primary electrolysis procedure that can be added to the hydrolysis reaction products discussed herein. Obtain a suitable container and substantially fill with warm water. Identify and procure a first and second conducting element that is operable to conduct electricity. Place a cover over the container wherein the cover includes to apertures so as to allow the first and second conducting element to be journaled therethrough. Connect the first and second conducting element to a battery. Subsequent connection of both battery terminals electrolysis will begin as evidenced by bubble production. Add an electrolyte to the water in the beaker. Additionally, add sodium to the water to accelerate the process. Execute process to completion.

It is further contemplated within the scope of the present invention that the silicon dioxide formulation and method of manufacture 100 could be employed as a key ingredient to food supplements, nutritional supplements, whole cell treatment systems, environmental solutions, drinks and others in order to facilitate eradication of bacteria, toxins, parasites, fungus and viruses. It should be further understood within the scope of the present invention that the silicon dioxide formulation and method of manufacture 100 could further have incorporated thereinto various trace metals wherein the trace metals incorporated are dependent upon the application of the silicon dioxide formulation and method of manufacture 100. The silicon dioxide of the present invention has a silicon source of zeolites and clays. It should be further understood within the scope of the present invention that the trace minerals are employed as nano-emulsions due to the advantages of small droplet size that contain elevated optical clarity and maintain physical constancy against gravitational partition and droplet accumulation. The aforementioned leads to improved bioavailability of the silicon dioxide formulation and method of manufacture 100, which leads to their suitability for food and drug applications.

It is further contemplated within the scope of the present invention that the silicon dioxide formulation and method of manufacture 100 include nano-encapsulation of the trace minerals, vitamins and silica incorporated therein. Nano-encapsulation provides the most favorable technique for ensnaring bioactive chemicals which can lead to further product development in fields such as but not limited to agri-food and nanotechnology. Additionally, it is contemplated within the scope of the present invention that the silicon dioxide formulation and method of manufacture 100 can utilize silica nanoparticles for controlled release applications in areas such as but not limited to suncare, nutritional supplements, animal care and environmental products. Through utilization of a reaction of tetramethylorthosilicate (TMOS) inside water droplets via production of a water and oil emulsion under both acidic and basic conditions. The aforementioned is accomplished through the addition of TMOS to a micro-emulsion resulting in the formulation of silica as TMOS which will reside in the oil phase of the aforementioned emulsion through diffusion from the water droplets. Once in the hydrophilic domain hydrolysis occurs rapidly due to the high concentration of water. The pH of the water droplets can broadly vary from one to eleven however variation of the pH diminishes the hydrolysis reaction of TMOS. If the aforementioned occurs, formation of a dense silica network will result that can be stabilized by a water/surfactant layer added during the formation.

It is further contemplated within the scope of the present invention that the an additional step of mixing hypochlorite or hypochlorous acid could be employed. Accomplishment would be executed by utilizing whole bacterial cell, with addition of microbial enzymes such as but not limited to cyanuric acid hydrolase, encapsulated in an inert silica matrix containing an amine group. The amine group functions to permeabilize the cell membrane and accelerate cyanuric acid production. This application would provide benefits in areas of cost reduction as well as lend practicality to whole cell treatment systems.

Atomic layer deposition is a powerful is a powerful deposition technique for constructing uniform, conformal, and ultra thin films in microelectronics, photovoltaics, catalyst, energy storage, and conversion. The possibility pathways for silicon dioxide atomic layer deposition using silicon tetrachloride and water without a catalyst can be employed within the scope of the present invention. The results show that the silicon tetrachloride has a half reaction is a rate determining step of Si—Cl/O—H binds and forming H—Cl bond. The water half-reaction undergoes hydrolysis in condensation processes, which are similar to conventional chemical vapor deposition. In the water half reaction, a large quantity of half reactions are present, and a multitude of water molecules are absorbed on the surface, which results in water assisted hydrolysis of Cl terminated surface and as such accelerates the water reaction. These techniques can be used to improve methods for the preparation of silicon dioxide atomic layer deposition and water based atomic layer depositions of other oxides.

In the preceding detailed description, reference has been made to the accompanying drawings that form a part hereof, and in which are shown by way of illustration specific embodiments in which the invention may be practiced.

These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A method of manufacturing a formulation containing water-soluble silicon dioxide fragments wherein the formulation is configured to provide intracellular detoxification wherein the method of manufacturing the formulation comprises the steps of:

(i) preparing a first reaction mixture, wherein the first reaction mixture if comprised of silicon dioxide, water and phosphoric acid;

(ii) heating the water of the first reaction mixture, wherein the water of the first reaction mixture is heated to 150-200 degrees Fahrenheit;

(iii) adding silicon dioxide to the first reaction mixture;

(iv) agitating the first reaction mixture;

(v) dispensing into the first reaction mixture a material wherein the material is selected from one of the following: quartz, silica, silicic oxide or crystalline silica;

(vi) adding phosphoric acid to the first reaction mixture;

(vii) agitating the first reaction mixture, wherein the agitation of the first reaction mixture occurs when the first reaction mixture is maintained at a temperature between 125 to 175 degrees Fahrenheit;

(viii) cooling the first reaction mixture, wherein the first reaction temperature is cooled to an ambient room temperature for 24 hours;

(ix) allowing the first reaction mixture to settle, wherein the first reaction mixture will settle and produce a first liquid layer and a first solid layer;

(x) separating the first liquid layer from the first reaction mixture, wherein the first liquid layer contains 1 to 25 mg/mL of solids;

(xi) preparing a second reaction mixture, wherein the second reaction mixture utilizes the first solid layer of the first reaction mixture;

(xii) adding silicon dioxide, phosphoric acid and water to the first solid layer of the first reaction mixture;

(xiii) heating the second reaction mixture;

(xiv) cooling the second reaction mixture;

(xv) settling the second reaction mixture, wherein the second reaction mixture separates into a second liquid layer and a second solid layer;

(xvi) separating the second liquid layer from the second reaction mixture;

(xvii) combining the first liquid layer from the first reaction mixture with the second liquid layer from the second reaction mixture to produce a final mixture, wherein the pH of the final mixture is 4.5 to 5.5; and (xviii) wherein the final mixture is suitable for human consumption.

2. The method of manufacturing the formulation containing water-soluble Silicon dioxide fragments as recited in claim 1, wherein the formulation further includes water-soluble hydrolyzed silicon dioxide fragments combined with a dietary supplement.

3. The method of manufacturing the formulation containing water-soluble Silicon dioxide fragments as recited in claim 2, wherein the dietary supplement is selected from a group consisting of: vitamins, minerals, fiber, fatty acid, amino acid, herbs or herbal extracts.

4. The method of manufacturing the formulation containing water-soluble Silicon dioxide fragments as recited in claim 3, wherein the formulation includes water-soluble hydrolyzed silicon dioxide fragments that are complexed with a metal ion.

5. The method of manufacturing the formulation containing water-soluble Silicon dioxide fragments as recited in claim 4, wherein the metal ion is selected from a group consisting of: sodium, magnesium, iron, cobalt, copper, zinc, manganese, molybdenum or selenium.

6. The method of manufacturing the formulation containing water-soluble Silicon dioxide fragments as recited in claim 5, wherein the formulation includes water-soluble hydrolyzed silicon dioxide fragments prepared by a process combining hydrolyzed silicon dioxide and phosphoric acid.

7. The method of manufacturing the formulation containing water-soluble Silicon dioxide fragments as recited in claim 6, wherein formulation further includes a mineral or vitamin selected from a group consisting of: selenium, zinc, sulfur, iron, vitamin B, vitamin C, vitamin E, vitamin D or retinol.

8. The method of manufacturing the formulation containing water-soluble silicon dioxide fragments as recited in claim 1, wherein the formulation is provided in liquid capsules, slurry form, gels or syrups.

* * * * *